US008535061B2

(12) United States Patent
Boutchko et al.

(10) Patent No.: US 8,535,061 B2
(45) Date of Patent: Sep. 17, 2013

(54) HUMAN TORSO PHANTOM FOR IMAGING OF HEART WITH REALISTIC MODES OF CARDIAC AND RESPIRATORY MOTION

(75) Inventors: Rostyslav Boutchko, Berkeley, CA (US); Karthikayan Balakrishnan, Vernon Hills, IL (US); Grant T Gullberg, El Cerrito, CA (US); James P O'Neil, San Leandro, CA (US)

(73) Assignee: The Regents of the University of California, Oakland, CA (US)

( * ) Notice: Subject to any disclaimer, the term of this patent is extended or adjusted under 35 U.S.C. 154(b) by 820 days.

(21) Appl. No.: 12/630,818

(22) Filed: Dec. 3, 2009

(65) Prior Publication Data

US 2010/0167251 A1 Jul. 1, 2010

Related U.S. Application Data

(63) Continuation-in-part of application No. PCT/US2009/065692, filed on Jun. 3, 2008.

(60) Provisional application No. 60/941,685, filed on Jun. 3, 2007.

(51) Int. Cl.
*G09B 23/28* (2006.01)

(52) U.S. Cl.
USPC .......................... 434/267; 434/262; 434/272

(58) Field of Classification Search
USPC ................ 434/262, 265, 267, 272; 600/508, 600/521
See application file for complete search history.

(56) References Cited

U.S. PATENT DOCUMENTS

| | | | | |
|---|---|---|---|---|
| 3,310,885 | A * | 3/1967 | Alderson | 434/267 |
| 4,167,070 | A * | 9/1979 | Orden | 434/272 |
| 4,894,013 | A * | 1/1990 | Smith et al. | 434/268 |
| 5,055,052 | A * | 10/1991 | Johnsen | 434/265 |
| 5,295,835 | A * | 3/1994 | Scheinberg et al. | 434/265 |
| 6,234,804 | B1 * | 5/2001 | Yong | 434/267 |
| 2002/0061503 | A1 * | 5/2002 | Chamberlain | 434/267 |
| 2002/0117173 | A1 * | 8/2002 | Lynn et al. | 128/202.28 |
| 2003/0091967 | A1 * | 5/2003 | Chosack et al. | 434/262 |
| 2004/0033477 | A1 * | 2/2004 | Ramphal et al. | 434/272 |
| 2004/0126746 | A1 * | 7/2004 | Toly | 434/262 |
| 2005/0214727 | A1 * | 9/2005 | Stoianovici et al. | 434/262 |
| 2006/0004281 | A1 * | 1/2006 | Saracen | 600/414 |

* cited by examiner

*Primary Examiner* — Xuan Thai
*Assistant Examiner* — Bruk Gebremichael
(74) *Attorney, Agent, or Firm* — Michelle Chew Wong; Lawrence Berkeley National Laboratory

(57) ABSTRACT

A human torso phantom and its construction, wherein the phantom mimics respiratory and cardiac cycles in a human allowing acquisition of medical imaging data under conditions simulating patient cardiac and respiratory motion.

14 Claims, 13 Drawing Sheets

A. 3D model of heart

Point sources
(anion exchange resin)

B

| | h (cm) | r (cm) |
|---|---|---|
| Interior | 8.5 | 1.75 |
| Exterior | 8.5 | 2.75 |

CT images (same slice) of phantom prototype at different stages of respiration

End Expiration

End Inspiration

HUMAN TORSO PHANTOM FOR IMAGING OF HEART WITH REALISTIC MODES OF CARDIAC AND RESPIRATORY MOTION

CROSS-REFERENCE TO RELATED APPLICATIONS

This application is a continuation-in-part of International Patent Application PCT/US2008/065692, filed on Jun. 3, 2008, which claims priority to U.S. Provisional Patent Application No. 60/941,685, filed on Jun. 3, 2007, both of which are hereby incorporated by reference in their entirety.

STATEMENT OF GOVERNMENTAL SUPPORT

This invention was made during work supported by Grants R01-HL71253, R01-EB00121 and R01-HL50663 awarded by the National Institutes of Health and under Contract No. DE-AC02-05CH11231 awarded by the U.S. Department of Energy. The government has certain rights in this invention.

BACKGROUND OF THE INVENTION

1. Field of the Invention

The present invention relates to a human torso phantom for modeling and imaging cardiac and respiratory motion.

2. Related Art

The goal of creating a torso phantom is to have an anthropomorphic tool for research of cardiac and respiratory motion in nuclear (e.g., single photon emission computed tomography (SPECT) and positron emission tomography (PET)) imaging, x-ray computed tomography (CT), magnetic resonance imaging (MRI) and in radiation therapy apparati. The most popular tool used for this purpose in nuclear cardiac imaging now, Jaszczak dynamic phantom, described in U.S. Pat. No. 6,629,469, hereby incorporated by reference in its entirety, has a rigid torso and lungs thus it cannot model respiratory motion. Also, the heart in the Jaszczak phantom is made in such manner that it cannot reproduce the twisting motion of the left ventricle. A recently presented phantom developed at URobotics Laboratory at John Hopkins University claims to model respiration but does not complement it with heart motion (Poster presentation M06-355 by Kenneth H. Wong et al, IEEE MIC 2006. <URL: http://www.nss-mic.org/2006/>.

Thus, there is a need for a human torso phantom which models human cardiac and respiratory motion.

BRIEF SUMMARY OF THE INVENTION

The present invention provides a human torso phantom useful for modeling the human heart, organs and respiratory motion for imaging studies and therapy and a simplified system for heart and lung motion control of the phantom.

In one embodiment, the present invention comprising an elastic deformable human torso phantom comprising: a) a non-rigid torso container containing (1) two lung-sized balloons, (2) a heart comprising two membranes comprised of non-uniform membrane material, having a smaller membrane inserted into the larger membrane, wherein the cavity and contents of the inner membrane represents the left ventricle and the cavity between the inner and outer membrane represents the myocardium tissue, (3) at least two sealable internal organs, wherein all the parts will be elastic, inter connected, encapsulated with a semi-rigid skeletal frame, and enclosed in the non-rigid container, wherein the container is filled with fluid and then sealed; b) fiducial markers attached to the top and other various positions of the torso container; c) system for heart and lung motion control comprised of (1) one pump for the heart and (2) either two pumps for lung inhalation and deflation or one pump and a compressed air tank, and further comprising (3) a control box with controllable switches connected to a computer containing the software to control the control box and collect the R-wave signal generated by the heart pump. Both cavities of the heart and the internal organs can be filled with radioactive fluid of controllable concentrations, thereby allowing for modeling different uptake levels of each organ independently.

In another embodiment, the phantom further comprising: (4) a thick tube modeling human aorta allowing controlled flow of variable speed and direction. In another embodiment, the phantom wherein each of the principal internal components of the phantom (both compartments of the heart, lungs, internal organs) is individually connected to outside reservoirs having liquids (or gases for the case of lungs) containing contrast agents that can be dynamically delivered to the individual organs in the process of operating the phantom.

Thus, in another embodiment, the present invention comprising an elastic deformable human torso phantom comprising: An elastic deformable human torso phantom comprising: a) a non-rigid torso container containing (1) two balloons representing the lungs, (2) two membranes and a base fitted to the membranes representing the heart, said membranes comprising a non-uniform polymer, wherein one membrane is smaller and inserted into the larger membrane and the base seals the membranes to form an inner cavity in the inner membrane and an outer cavity between the inner and outer membrane, such that the inner cavity and contents of the inner membrane represents the left ventricle and the outer cavity between the inner and outer membrane represents the myocardium tissue, wherein the outer cavity filled with a porous filling, (3) an elastic tube modeling the aorta, and (4) at least two additional internal organs, wherein all the parts are elastic, mechanically interlinked, connected to the control center, encapsulated with a semi-rigid skeletal frame, and enclosed in the non-rigid container, wherein the container is filled with fluid and then sealed; b) fiducial markers and/oror radiation dosimeters attached to the surface of the torso and other various positions inside the torso container; c) system for controlled dynamic delivery of contrast agents to each of said internal organ models comprising a plurality of pumps and valves, connecting outside containers with contrast agents to the corresponding internal organs; and d) system for heart and lung motion control comprising one pump for the heart and either two pumps for lung inhalation and deflation or one pump and a compressed air tank, and further comprising a control box with controllable switches connected to a computer containing the software to control the control box and collect the R-wave signal generated by the heart pump.

Both cavities of the heart and the internal organs can be filled with radioactive fluid of controllable concentrations, thereby allowing for modeling different uptake levels of each organ independently.

It is one object of the invention to provide the phantom as an anthropomorphic tool for research of cardiac and respiratory motion in imaging using such techniques including but not limited to imaging such as SPECT and PET, x-ray computed tomography, magnetic resonance imaging, ultrasound, or other medical imaging techniques. Specific applications for imaging and multi-modality imaging are also provided.

In one aspect, the present invention provides technological solutions of a combination of respiratory and cardiac motion in one phantom. Anatomy measurement in the presence of motion, continuous motion imaging and dynamic or static imaging of combined respiratory and cardiac motion are also provided.

In another aspect, the phantom provides modeling of kinetic processes in different tissues by controlled dynamic delivery of contrast agents to different tissues represented in the phantom. Contrast agents include any compounds that are highly visible with a specific imaging modality, for example radioactive isotopes in nuclear imaging, gadolinium or boron in x-ray CT, paramagnetic fluids or fats in MRI etc. Combinations of different contrast agents can be used simultaneously to facilitate muldimodality regietration. Contrast agents are delivered independently to each of the organ models in the phantom.

In another aspect, the phantom provides technological solutions modeling of blood flow in aorta and other large blood vessels for MR or CT imaging of flow in the body both in a static configuration or in combination with respiratory and/or cardiac motion of the phantom.

In yet another aspect, the phantom provides modeling twisting in heart motion and realistically elastic and non-uniform, yet controllable, motion of all internal organs. In one embodiment, the non-uniform membrane material of both inner and outer membranes of the heart further comprising four ridges 2 to 4 times thicker than the rest of the membrane covering the heart in a spiral manner and completing one full rotation around the membrane, to promote the twisting motion of the heart to simulate cardiac motion in vivo.

In another aspect, tracking heart motion using fiducial markers positioned directly on the heart surface is provided and a multi-modality fiducial marker system that allows motion tracking and inter-modality registration for SPECT, PET and CT is described. Multi-modality for medical imaging is further described.

In another aspect, real time dosimetry in the presence of respiratory and cardiac motion is provided using insertable dosimetry devices for the purpose of radiation therapy planning experiments.

DETAILED DESCRIPTION OF THE PREFERRED EMBODIMENT

Figure 1A:
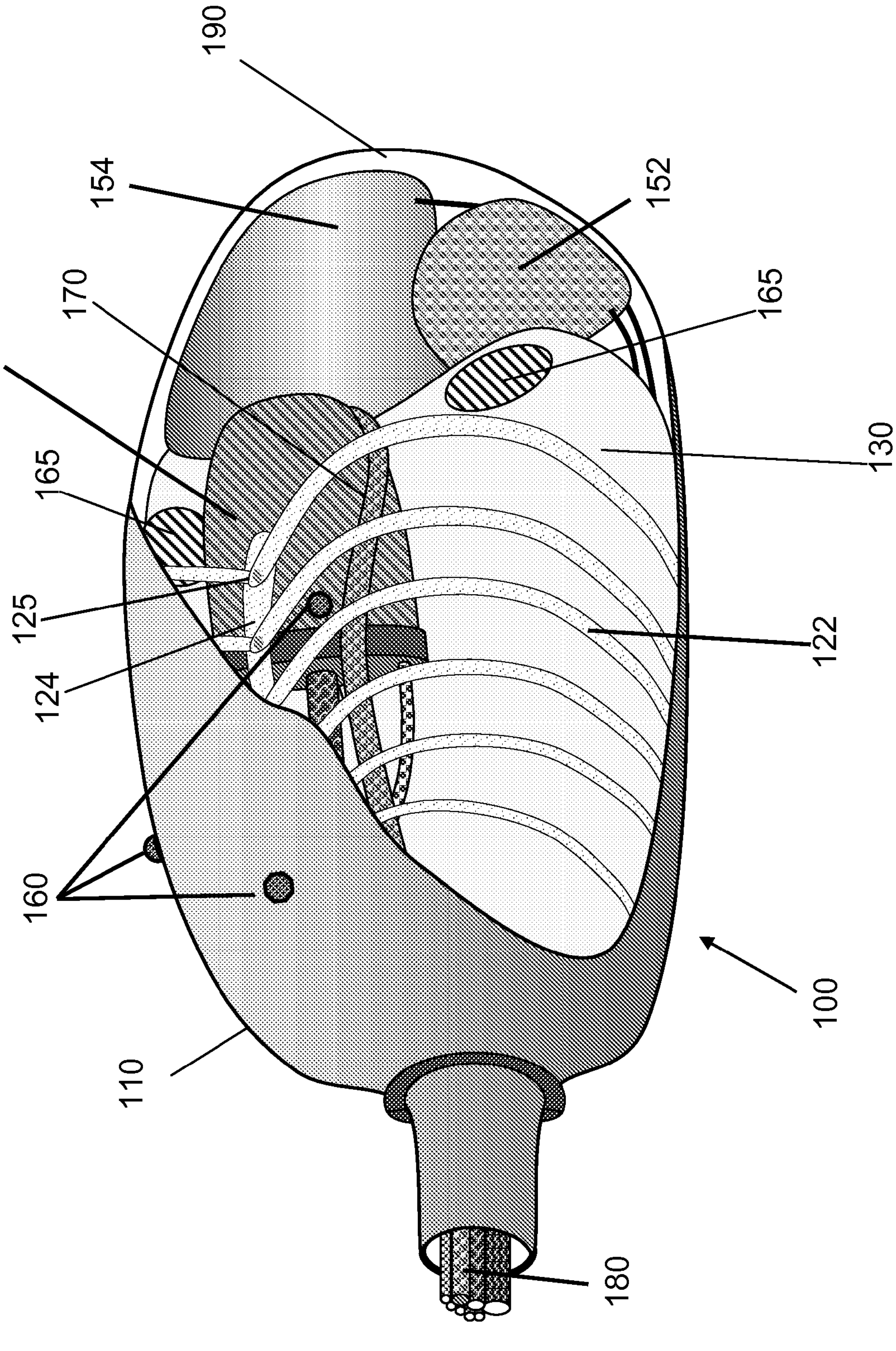
FIG. 1A) show a cartoon ofows the elastic deformable torso phantom 100 showing the main structural parts and having an expanded list of organ models (e.g., heart, lungs, aorta, liver, intestines/stomach) and ducts (air, blood, myocardial contrast inlet/outlet, aorta, liver and stomach/intestine).

Herein is described a human torso phantom to provide an anthropomorphic tool for research of cardiac and respiratory motion in nuclear (SPECT and PET) imaging and CT, MRI, ultrasound or other imaging techniques. As used herein and known in the art, SPECT is abbreviated for single photon emission tomography, CT for x-ray computed tomography, MRI for magnetic resonance imaging and PET for positron emission tomography.

in one embodiment, the phantom 100 as schematically shown in FIG. 1A. The phantom 100 comprises an elastic casing 110, containing the rest of the phantom and filled with water (with or without contrast agents added). The elastic casing 110 contains several individually sealable cavities, casings or pouches representing lungs, heart and internal organs. Collapsible anthropomorphic minimally-attenuating 2-liter rubber lungs (e.g., rubber balloons) 130 enclosed together with the heart 140 in an optional additional elastic casing (not shown in FIG. 2A) representing the pleural cavity 190. This cavity is enclosed in a semi-rigid skeletal frame 220 with rigid plastic ribs 222, spine 223 and sternum 224, joined with elastic connectors 225 acting as elastic connecting tissue in the same manner as in the real ribcage. The whole phantom 100 is enclosed in an elastic shell 110 representing a human torso. An elastic tube 170 simulating the aorta and two elastic pouches to mimic the other internal organs such as the liver and bladder in the human body can be individually filled with liquid solutions, and optionally a contrast agent, with the ability to change the contrast concentration in real time. On the surface of the torso, position markers 160 are installed on the casing 110 in order to trace the motion with time. A set of liquid and air conduits or tubing 180 connecting the lungs, the heart, the aorta and the internal organs to the appropriate pumps also lead to/from the phantom.

As used herein, a "contrast agent" is a chemical compound that substitutes or is added to the liquid or gas that fills different phantom components in order to make the liquid or gas visible to the medical scanner of the selected imaging modality. For example, in nuclear imaging, different radioactive isotopes are used such as technetium-99m or thallium-201 in SPECT, fluorine-19, carbon-11, nitrogen-13 etc. in PET. In x-ray CT, contrast agents are typically a solution of a compound with large x-ray scattering cross-section such as gadolinium or iodine. In MRI, paramagnetic compounds are used, gadolinium being the most typical. Helium-3 can added to compressed air as an gaseous MR contrast agent. In medical sonography, microbubbles are used. Contrast agents can be used individually or in combination, E.g. radioisotope can be combined with gadolinium for SPECT/CT or PET/CT.

"Markers" such as "fiducial markers" or "motion markers" 160 are used interchangeably and refer to small objects used in or on the phantom that will be used track motion, concentration, flow, or other phantom characteristic in an imaging modality. These objects should be readily identifiable using a particular imaging modality. Marker material depends on the modality. For examples, point radioactive sources are used for PET and SPECT, dense objects for X-ray CT, vitamin E capsules for MRI. Multi-modality markers are possible, for example a CT-SPECT markers is comprised of a sealed radioactive source embedded in a dense plate.

Controls of respiratory and cardiac motion are independent. In one embodiment, non-uniform respiratory motion is achieved by pumping air in and out of lungs using a combination of a compressed-air tank and an external pump with controlled volume and timing of airflow as in FIG. 3. Realistic relative motion of the organ models will be achieved through interaction of the semi-rigid skeletal frame and fully elastic abdominal cavity.

In a preferred embodiment, the lungs 130 will be shaped anatomically according to typical human sized lungs. In another embodiment, other organs shaped anatomically correct are included in the phantom.

In a preferred embodiment, the phantom is constructed such that it can be opened up (e.g., with a zipper or other resealable seal), filled with water, sealed only with pipes or tube-like structures 180 sticking out of neck, having all the organs sealed. If needed, openings can be provided on the side of the torso to insert other organs and resealed.

Any number of elastic materials can be used for the construction of the phantom parts, including but not limited to, rubber, vinyl, latex, silicone, polymers, and combinations thereof. For example, one prototype of the phantom was constructed using elastic sheet rubber, balloons and hot-water bottles immersed in water in a rigid vinyl tub. During the cardiac simulation studies of this prototype, the results of an X-ray CT-scan illustrated a basic required feature of the deformable phantom are non-uniformity of deformations and possibility of motion tracking using position markers. Information about the trajectory of the position markers will be used to accommodate application of the proposed motion compensation reconstruction algorithms.

Figure 1B:
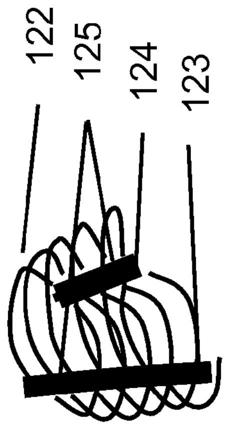
FIG. 1B is a separate drawing of the ribcage, showing rigid spine, rib and sternum bones, mutually connected with elastic material to allow for breathing.
Figure 1C:
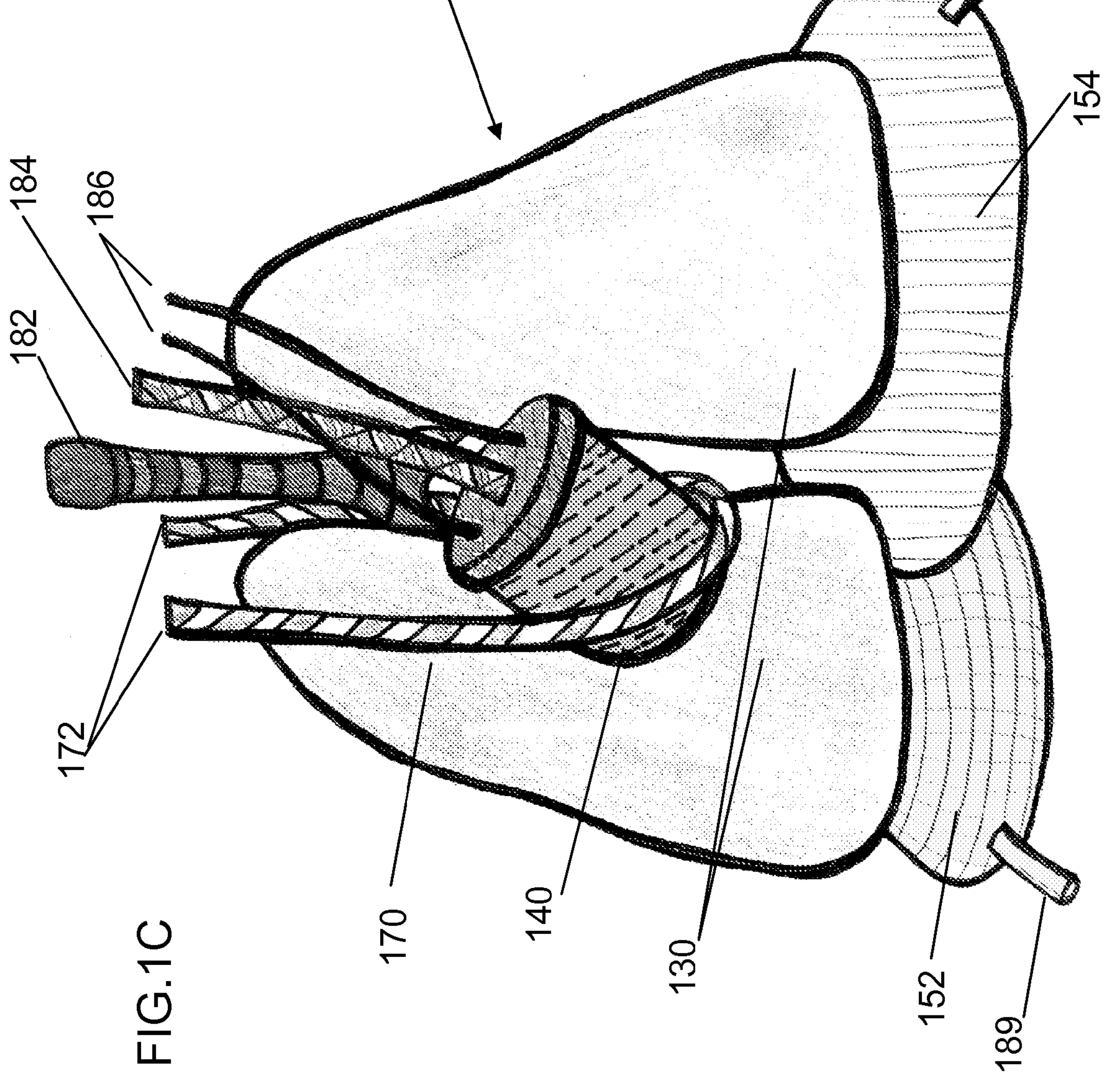
FIG. 1C is a cartoon showing the internal structure of the torso phantom 200.

In another embodiment, the phantom as schematically shown in the phantom 100 shown in FIGS. 1A-1C. Referring now to FIG. 1A showing the general structure of the phantom 100, the phantom comprising an outer shell 110, having an interior space filled with aqueous solution and an internal structural representing the ribcage 120, internal organ models, a set of air and liquid ducts 180 connected to the internal organ models, and optionally a control for real time flow control of the ducts.

In one embodiment, the outer shell 110 is preferably made of a polymer such as a thermoplastic elastomer or polyethylene. The ribcage should be have elastic properties and can be made of materials such as rubber or polyurethane. In another embodiment, the organs are connected to the ribs or sternum as occurs anatomically in a human torso. Internal model organs include heart 140, lungs 130, aorta 170, liver 152 and intestines 154. The set of air and liquid ducts 170 and 180 connect to the different organs and a control of the ducts can include such controls as compressed air tank, air pump, valve boards, liquid pump(s), valves and liquid tanks (elevated or pressurized if needed) for liquid delivery and control in the internal organs, Pump and valve operation can be controlled by a central computer console or pneumatically.

Referring now to FIG. 1C showing the internal structure of the phantom 100, the heart 140 can be elastic, expandable, filled with two types of liquid with or without contrast agents, pressurized. The lungs 130 are elastic, expandable, filled with pressurized air or other gas to be used as contrast agent (e.g., $He^3$ for MR imaging). The aorta 170 or other large (e.g., ~1 cm diameter) blood vessel for flow measurements should have constant volume, filled with static or flowing liquid with or without a contrast agent, not connected to the heart. Variable diameters can be used to model varying normal or diseased states such as stenosis. The liver 152 should have constant volume, filled with liquid with optional contrast agent. The intestines/stomach 154 should also have constant volume, and filled with liquid with optional contrast agent. In addition to internal organ models of the heart 140, lungs 130, aorta 170, liver 152, stomach/intestines 154, the phantom includes an expanded set of air and liquid ducts leading to different organs, with or without real time flow control. In FIG. 1C, the air duct 182 is connected to the lung 130, with two-way flow driven by compressed gas with controlled valves and a pump (shown in FIG. 4) for faster air outlet and used to achieve specified static phase or to model controlled breathing. A blood duct 184 is two-way flow driven by liquid pump, and used to achieve static phases or to model cardiac motion. Myocardial contrast inlet/outlet ducts 186 can also be used for real-time delivery of contrast agent to the (constant volume) myocardial cavity. The aorta duct 172 can be used to deliver contrast agents to the aorta 170 and, if needed, maintain constant-speed flow. The liver duct 189 can be used for contrast delivery, can be doubled and a stomach/intestine duct 188 can be used for contrast delivery as well.

Figure 2:
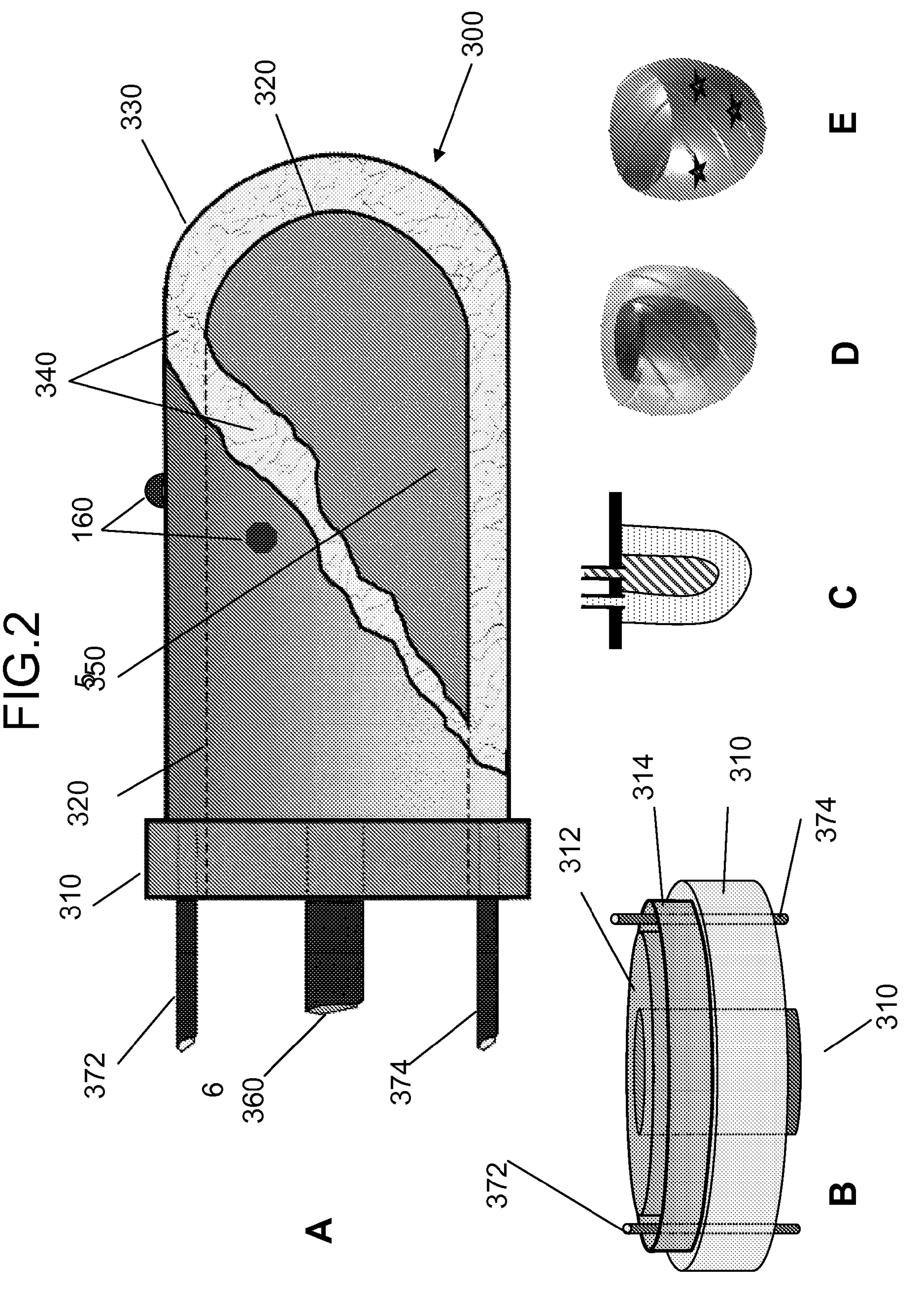
FIG. 2A shows a side view of the base of the heart insert 300.
FIG. 2B shows a longitudinal cross-section of a heart insert 300.
FIG. 2C shows a cartoon of an elastic heart 300 with two ellipsoid-shaped walls. Myocardium is represented by the liquid enclosed between the inner and the outer walls. Heart beating is caused by pumping liquid into the inner cavity.
FIG. 2D shows a cartoon of an elastic heart with both inner and outer walls molded from elastic material to be non-uniform with spiral pattern so to reproduce realistic twisting of the heart during expansion.
FIG. 2E shows a cartoon of an elastic heart with point sources attached to the outer wall of the elastic heart insert.

The elastic beating heart insert 140 is shown in more detail in FIG. 2. As shown in FIG. 2C, the elastic beating heart 40 has inner and outer membranes, comprised of elastic membrane material such as latex or sheet rubber. The smaller inner membrane is inserted into the larger membrane, wherein the cavity and contents of the inner membrane represents the left ventricle and the cavity between the inner and outer membrane represents the myocardium tissue. Thus the heart 140 has an inner and outer cavity, both cavities filled with fluid, each capable of having different contrast agent concentration and accessed individually.

In another embodiment, the heart insert 140 is as shown in detail in FIG. 2(*a*) and (b). The base 310 of the heart insert 140 (also shown separately, top view in FIG. 2*b*) comprising polymeric materials, such as latex of sheet rubber, formed as extensions for attaching to elastic inserts 312 and 314 and fitted to the inner membrane 320 and the outer membranes 330 of the heart insert to seal the membranes to form the heart with an inner cavity 350 representing the left ventricle and outer cavity 340 representing the myocardium tissue. Holes are made for delivering contrast agent and pressure to both the (myocardium) outer cavity 340 and the inner left ventricle cavity 350. The inner membrane 320 may have a diameter ~5-6 cm, and made of a polymer such as elastic latex or sheet rubber, which can be texturized (as shown in FIGS. 2*d* and 2*e*) if twisted motion modality of the heart insert is desired. The outer membrane 330 can be made of a polymer such as latex or thermoplastic elastomer, with Young's modulus at least twice lower than that of the inner shell. This is needed to ensure realistic extension during the heartbeat. The cavity 340, between the inner membrane 320 and the outer membrane 330 is preferably filled with a porous filling to model the mechanical properties of the muscle tissue of the myocardium. The porous filling can be any material that is porous such as elastic string, mesh or other polymeric or layerable material 350, bundled to create bulk volume in such a manner that at least 60% of the cavity can be filled with liquid delivered through openings 372 and 374. The volume of the myocardial cavity 340 remains constant throughout the experiment, the thickness can change but minimal thickness of 0.5 cm is maintained by the presence of the filling. Left ventricular inner cavity should have constant volume, pressurized and pumped through 360. Left ventricular blood inlet 312, inlet 312 and outlet 314 can be used for user-guided real time delivery of the myocardial contrast material to the cavity 340.

In one embodiment, cardiac motion is achieved by pumping of liquid into the inner cavity of the elastic heart. Both inner and outer membranes of the heart 140 are made from non-homogeneous elastic material such as rubber, and structured as shown in FIG. 2D to imitate the in vivo twisting motion of the heart. The non-homogeneity of the heart membrane material is manifested by millimeter-wide ridges 2 to 4 times thicker than the rest of the membrane, covering the heart in spiral manner. At least four ridges completing one full rotation around the membrane are suggested. At the initial stage, ridges can be substituted by rubber bands with cross section of about 2×0.5 mm to produce a cardiac twisting motion. This twisting motion is incorporated following a simulation study done in our group and described in Rohmer D, Sitek A, Gullberg GT: Simulation of the beating heart based on physically modeling a deformable balloon. Lawrence Berkeley National Laboratory Publication, LBNL-60664, Jul. 18, 2006, hereby incorporated by reference.

Figure 5:
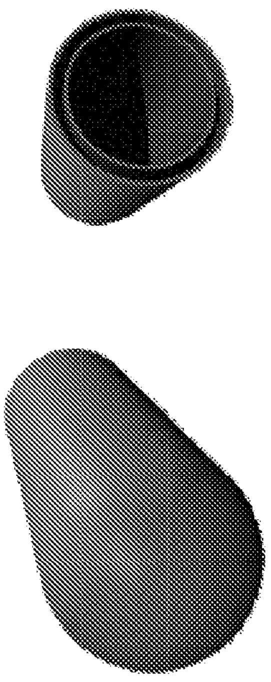
FIGS. 5A and 5B show a three-dimensional model of the beating heart that can be used in the present phantom and the dimensions.
FIG. 5C shows some preferred point sources for the heart in detail.
Figure 5:
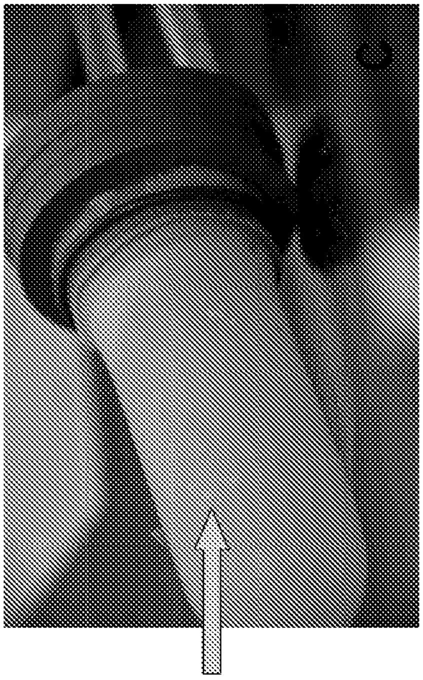
Figure 5:
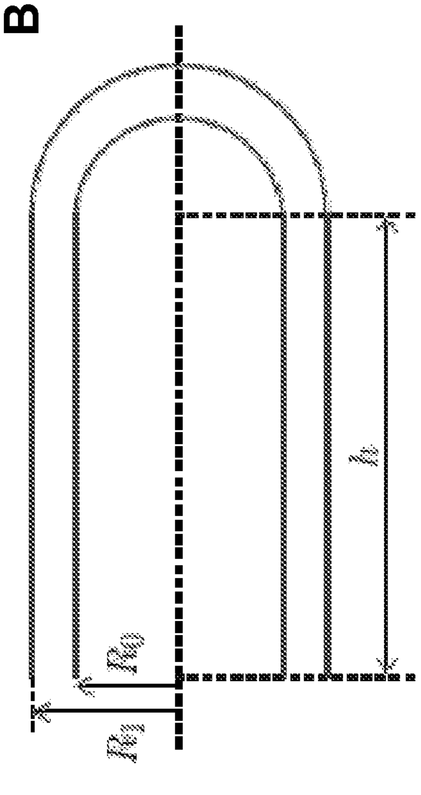

FIGS. 5A and 5B show a three-dimensional model of the beating heart that can be used in the present phantom and the dimensions. Fiducial markers are placed on the heart surface as schematically shown in FIG. 2E or as shown in FIG. 5C. Both dynamic imaging (with motion) and snapshot imaging of any preset cardiac or respiratory phase are allowed.

Respiration will be modeled by pumping air in and out of the lungs 130. Changes in the lung volume will cause non-uniform variations in positions and, to lesser extent, shapes of the heart, internal organs and attenuating body.

In one embodiment, the phantom is further comprised of system for heart and lung motion control. The system comprising (1) one pump for the heart and (2) either two pumps for inhalation and deflation or one pump and a compressed air tank, and further comprising (3) a control box with controllable switches connected to a computer containing the software to control the control box and collect the R-wave signal.

Figure 3:
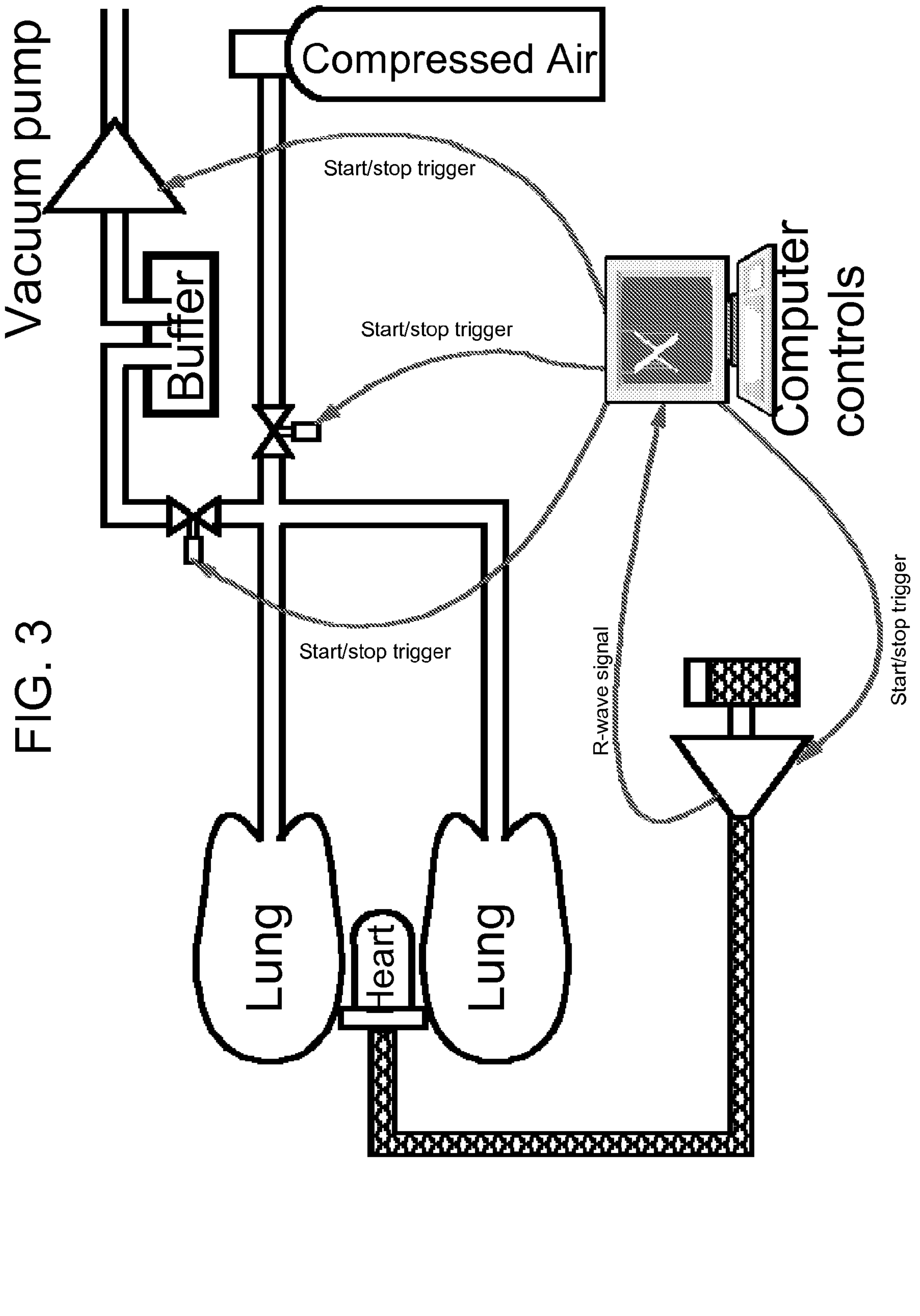
FIG. 3. Schematic of the experimental set-up of the control system of the phantom.

FIG. 3 shows a schematic of the experimental control set-up of the phantom. In one embodiment, the phantom controls are comprised of a pump to pump fluid into the heart; a limit switch on the pump to provide an R-wave trigger based on cardiac phase; a vacuum pump to collapse the lungs; solenoid valves to open/close the lungs to mimic respiratory motion by inflating the lungs; and computer controls to provide automation by sending trigger signals to the solenoid valves and pumps. Computer controls can be a laptop running control software such as LabVIEW. In other embodiments, any appropriate pump or a modified rodent-respirator is used to pump fluid into the heart.

Cardiac motion is achieved by controlled pump-induced change in the volume of the innermost cavity of the heart. In one embodiment, the inner membrane of the heart 40 is pumped with a modified rodent respirator having a control box. In another embodiment, any appropriate pump having a control box is used. Suitable settings for generating and modeling the heart twisting motion are the ejection volume of the pump should be able to pump up to 30 mL and simulate up to 200 beats per minute.

Figure 4A:
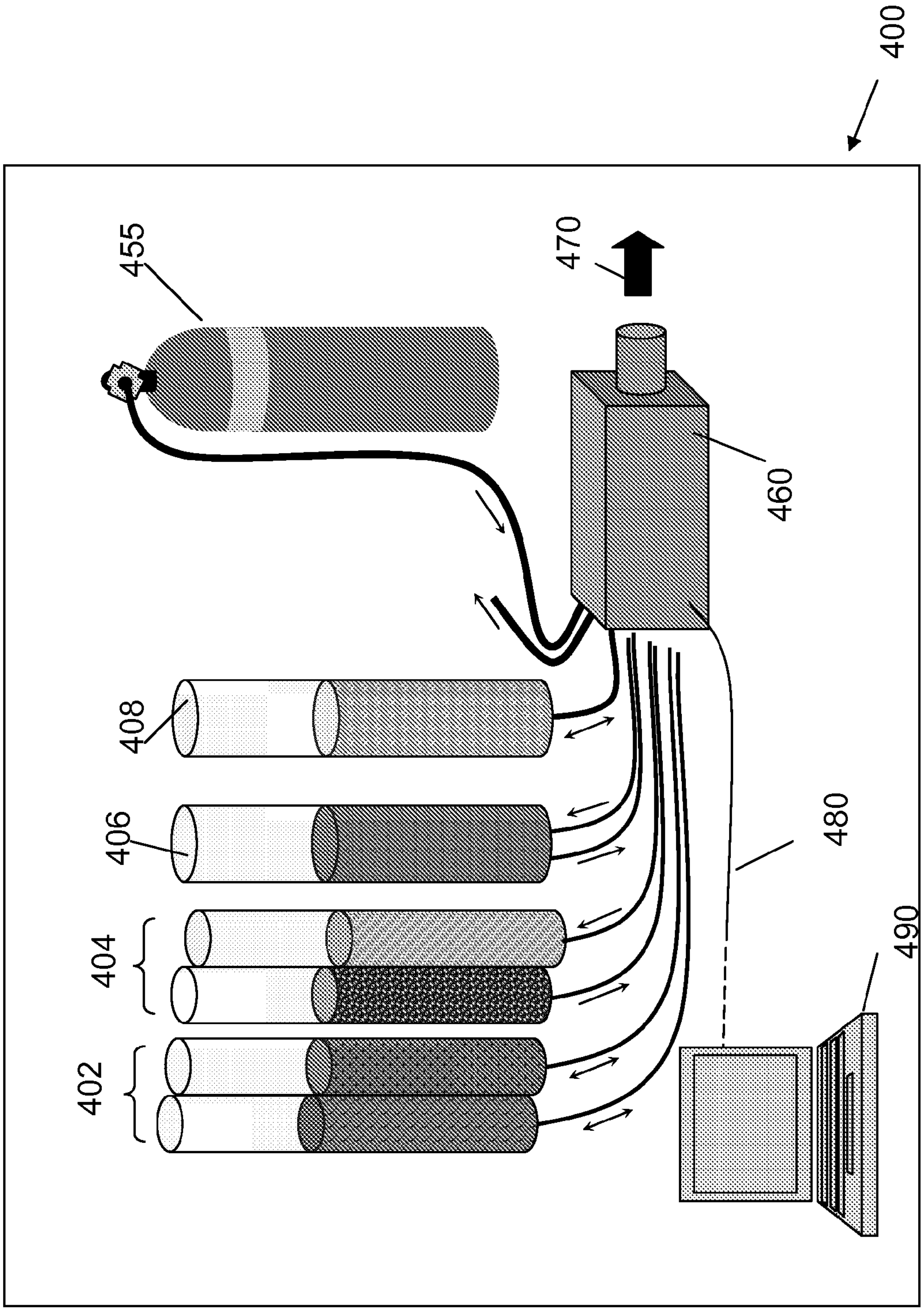
FIG. 4A shows a schematic of the imaging contrast control system 400.
Figure 4B:
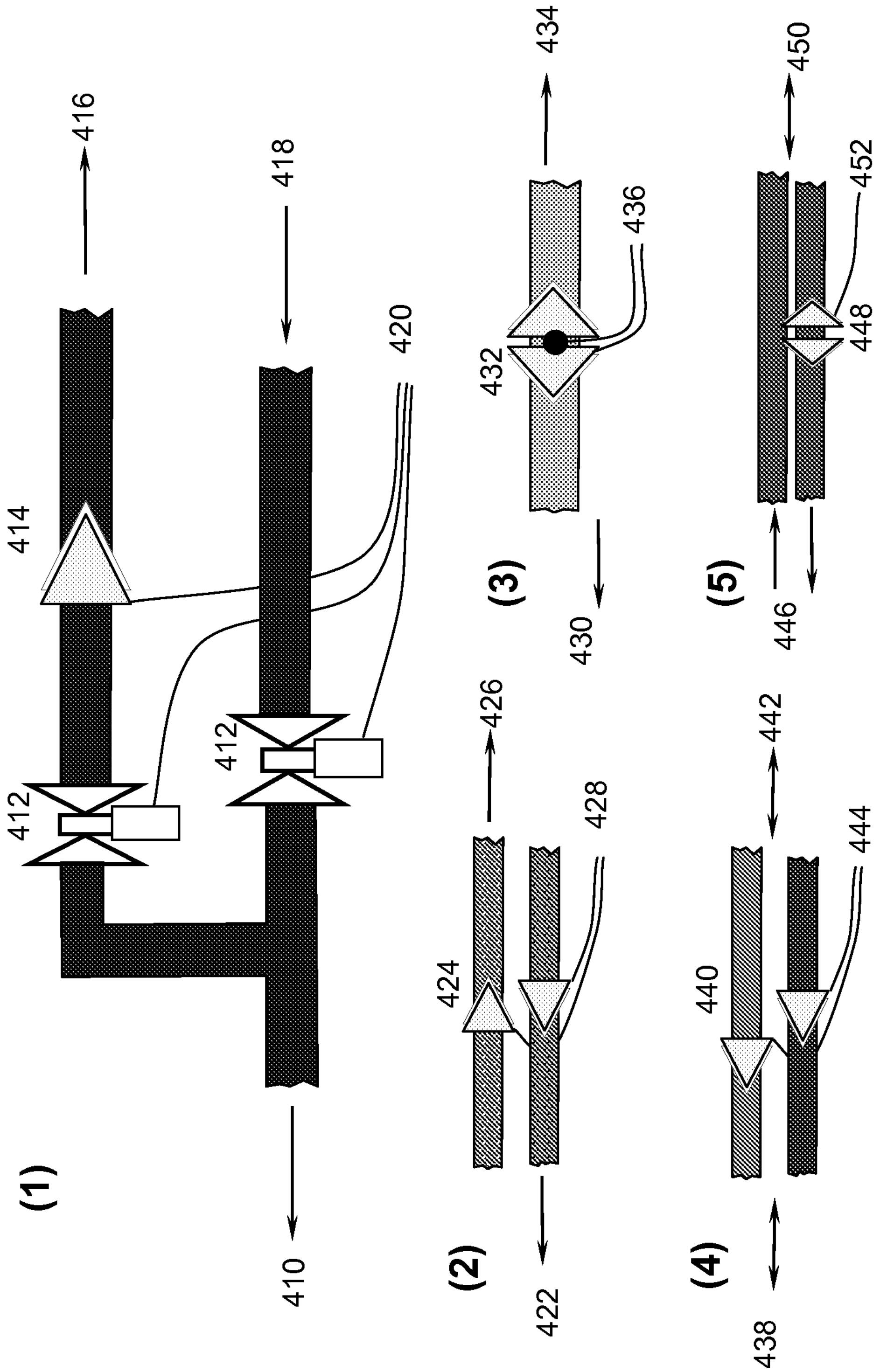
FIG. 4B is a schematic showing the mini-pump and valve control systems.

In another embodiment, the heart, inner organs and torso medium can be filled with liquids with different contrast agents. In one embodiment, the phantom further comprising imaging contrast controls. Referring now to FIG. 4, controlled dynamic delivery of contrast agents can occur using a system as shown. Reservoirs for the liquid solutions for each of the internal organs can be connected to the organs in the phantom through a control box 460 comprising a mini-pump and valve control unit shown in more detail in FIG. 4B. The control box 360 is connected to the phantom 100 by a connection 470 (not shown but represented by the arrow). In one embodiment, reservoirs 402 for each organ are connected through the control box 360 to the phantom 100 thereby allowing the organs to be regulated independently from each other. Only two reservoirs 402 are shown in FIG. 4A. Liquids filling the myocardium insert are connected through the control box 460 to input and output reservoirs 404 for the delivery of dynamic contrast agent concentration and optionally connected to an external system regulating concentration (not shown). Aorta liquid in reservoir 406 is connected to the control box to inlet and outlet tubes. Blood-modeling liquid used by the heart pump in container 408 can typically be realized as the inside of the heart pump. Also connected to the control box are a compressed air tank 455, plumbing connection 470 to the phantom 200, and connection 480 to a computer console 490. If $He^3$-enhanced MRI is considered, an additional He3 container can be connected.

Referring now to FIG. 4B, the miniature pumps, valves and control units can comprise controls for each organ. Such controls can be as shown. In FIG. 4(B)(1), Lung controls comprising a pipe to lungs 410, opening/closing valves working in counter-phase 412, minipump 414, pipe open to atmosphere 416, pipe to compressed air tank 418 and pneumatic or computer controls 420 to control the start/stop for valves and on/off for air pump. In FIG. 4(B)(2), Myocardium controls comprising inflow and outflow pipes 422 to myocardium cavity, identical minipumps 424 controlling dynamic flow, connection to inflow/outflow liquid tanks 426, and on/off pump controls 428. In FIG. 3(B)(3) Heart (left ventricle) controls comprising pipe 430 to the inner cavity of heart insert, two-sided pump 432, buffer 434 and on/off pump controls 436. In FIG. 4(B)(4) inner organ (e.g., liver/gall bladder) controls comprising pipes 438 to organs (potentially double pipes), minipumps 440 (if not double pipes, the minipumps are reversible), tanks with organ liquids 442, and pump on/off and direction controls 444. In FIG. 4(B)(5) Aorta control comprising two pipes to the two ends of the aorta 446. Reversible pump 448. Connections to aorta fluid tank 450 and pump on/off, direction and speed controls 452.

In one embodiment, fiducial markers 160 are used as small contrast markers that will be identifiable in imaging. Fiducial motion markers for inter-modality registration and for tracing the motion of the phantom and its parts. Both outside markers (connected to shell 110) and inside markers (connected to some of the organs) can be used. Typical marker diameter is 1-2 mm, but may be larger for multimodality markers.

Marker material depends on the medical imaging modality. For examples, point radioactive sources are used for PET and SPECT, dense objects for X-ray CT, vitamin E capsules for MRI. Multi-modality markers are possible and contemplated in the present invention. Fiducial markers can be small, usually spherical, objects comprising material best visible by the medical imaging modality of interest. For example, in one embodiment, the fiducial markers are radioactive point sources for nuclear medicine attached to the phantom and at various points detectable by multiple modalities, including but not limited to, SPECT, and PET cameras. Different radioisotopes can be used specifically for each type of camera. For CT, the fiducial markers would be high attenuation density materials such as heavy metals. For MR, the fiducial markers can be high contrast magnetic materials such as gadolinium$^{3+}$, manganese or iron oxide, or oral contrast agents including vitamin E capsules or barium sulfate.

In another embodiment, the phantom 100 further comprising tumor inserts 165. Such tumor models are useful for studying and imaging local dosimetry and evaluation of respiration gating in radiotherapy treatment planning. Tumors can be placed on the surface of the lung and other locations in or on the phantom prior to each experiment. Tumor inserts 165 can be made from materials or devices capable of radiation dosimetry. In one embodiment, X-ray film which can be cut into the needed shape and size. In another embodiment, the tumor insert 165 comprising a detector. Examples include silicone diode, CCD detectors, thermoluminescent or other dosimetry detector. In one embodiment, thermoluminescent detectors such as described in Bilski P, Waligárski M P, Budzanowski M, Ochab E, Olko P, Miniature thermoluminescent detectors for dosimetry in radiotherapy, *Radiat Prot Dosimetry.* 2002; 101(1-4):473-6, hereby incorporated by reference. Briefly, several types of miniature thermoluminescent LiF:Mg,Ti and LiF:Mg,Cu,P detectors specially designed for clinical dosimetry in radiotherapy can be used. The detectors are manufactured in the form of solid pellets of diameter down to 1 mm and typical thickness 0.5 mm, in various shapes (e.g., rods) with various diameters that are comparable to tumors found in patients (e.g., 0.5 mm and a length of a few mm), and as two-layer detectors with a thin (in the range of 0.065 mm) active layer of high-sensitive LiF:Mg,Cu,P and etc.

One challenge in fabricating the phantom are related to properties of the elastic media used to construct the individual organs and the torso enclosure. Shaping an anatomically exact organ of reliable strength is not always possible. Models and molds for each organ can be made as described by others and as is known in the art. For example, the lung balloons may be formed by preparing a solution by dissolving 50 parts of calcium nitrate tetrahydrate in 50 parts reagent alcohol. A latex dipping bath is also prepared by adding a wetting agent (0.1-0.25 pphr) and an antioxidant (1.0-3.0 pphr) to a pre-vulcanized, natural rubber latex. Aqueous dispersions of surfactants are acceptable as wetting agents, such as sodium lauryl sulphate, potassium oleate, or Darvan WAQ available from R. T. Vanderbilt Co., Inc., of Norwalk, Conn. and Octowet 70D available from Tiarco Chemical Co., of Dalton, Ga. Satisfactory aqueous dispersions of antioxidants of the non-discoloring, hindered-phenolic type include Octolite 640 available from Tiarco Chemical Co., Bostex 24 available from Akron Dispersions of Akron, Ohio, Akrosperse W-19119 available from Akrochem Corp. of Akron, Ohio, and Agerite Superlite available from R. T. Vanderbilt Co., Inc. The latex is a medium modulus, pre-vulcanized natural rubber latex such as Guthrie PVMM from Guthrie Latex, Inc. of Tucson, Ariz., Chemionics-960CX9949 from Chemionics Corp. of Tallmadge, Ohio, and Heveatex HA-1438/D710 from Heveatex Corp. of Fall River, Mass. The preferred components are Darvan WAQ, Agerite Superlite and Guthrie PVMM. Distilled water is added to the latex dipping bath until the total solids content is 55%. The compounded latex is matured at room temperature for about 48 hours, then filtered through a stainless steel 80-mesh sieve.

A lung-shaped, aluminum former is heated in air at about 70° C. for 30 minutes, dipped in the prepared solution for less than about 10 seconds, then dried in air at room temperature for 15 minutes leaving the former coated with a uniform gel of coacervant. The former is heated to facilitate solvent evaporation. The coated former is submerged in the latex dipping bath where it remains dwelled for about 5 to about 10 minute. The former is withdrawn from the latex at a rate of 1-2 mm per second. The resulting opaque, rubber gel is dried in air at about 21-23° C. for up to about 30 minutes. The former is leached in distilled water at about 40° C. to about 50° C. for 2 to 3 hours to remove non-rubber constituents and then dried in air at 50° C. for several hours until the rubber lung material becomes transparent. The lung material is then wet-stripped from the former, leached in distilled water at 30° C. for up to 24 hours to further remove remaining hydrophilic materials, then dried in air at 50° C. for several hours until transparency is restored. Finally, the lung is surface-treated by immersion in an aqueous chlorine solution (0.40 g Cl.sup.-/L water) at 21-23° C. for up to about 30 minutes. The lung may optionally be neutralized in a KOH/water solution (pH=8.5) at 21-23° C. for 5 minutes. In either case, the lung is rinsed in water at 21-23° C. for about 10 minutes, then dried in air at about 50° C. to about 70° C. for up to about 30 minutes. The resulting lung is transparent, amber, glossy, and tack-free.

Another challenge is correct pressurization of the heart 140 needed to avoid its deformation by the environment. The minimum pressure of the heart 140 should be at least 5% above that of the inside of the main cavity of the phantom (about 1.1 atmospheres). The maximum pressure will be determined by the elasticity and the volume of the heart membranes. Exact values of the minimum and maximum pressure in the heart will be determined by calibration for each specific phantom. It is important that the heart pump controlling the heart pressurization has sufficient power to sustain heart motion for extended period of time.

The evaluation of inter-modality image registration will be accomplished by performing physical phantom experiments. At present there is no phantom that simulates respiratory motion and cardiac deformation available for evaluation. The beating heart in the prior art dynamic cardiac phantoms simulate a pseudo cardiac motion observed in nuclear cardiac imaging but does not simulate deformation caused by twisting. The present phantom corrects both of these to allow accurate testing methods with more realistic physical data.

The phantom can mimic motion both on global (respiration and body motion) and local (cardiac) scales. At any cardiac or respiratory phase, the motion of the phantom can be stopped and a snapshot acquire of the given phase. Therefore, in addition to realistic acquisition with continuous controlled motion, the new phantom can be used to create a database as described below. Most methods simulate motion using some affine transformation simulated by linear bed and phantom translation. However, we describe an approach which collects a database that will be flexible enough to simulate various types of motion and cardiac deformation with physical data.

Thus, in another embodiment, the present phantom also allows the collection of data for a database. The approach here is similar to that in our recent publication, Sitek A, Reutter B W, Huesman R H, Gullberg G T: Method of generating multiple sets of experimental phantom data. J Nucl Med, 47:1187-1192, 2006, hereby incorporated by reference. In one embodiment, the new deformation phantom is used to acquire a database of SPECT sinograms and attenuation maps for different cardiac and respiratory phases. Emission data will be acquired with activity in the myocardium, liver, and background. Attenuation maps will be used to determine true distributions of activity in the phantom and to establish exact positions of the motion markers. To quantitatively access the quality of motion matching, emission data will first be reconstructed using perfectly registered CT-derived attenuation maps. These results will be compared with results obtained (1) with use of gated attenuation maps synthesized from two sets of CT images acquired at normal end-inspiration and end-expiration, and (2) with use of the average of the acquired and synthesized images. Using this approach, the SPECT-CT registration methods used with the phantom can be evaluated using a scanner such as the GE VG3 Millennium Hawkeye. The collection of the database may require several very short acquisitions resulting in longer data acquisition times. Careful registration will be required if the phantom is removed at any time.

In one embodiment, the phantom can be used as an anthropomorphic tool for research of cardiac and respiratory motion in imaging using such techniques including but not limited to medical imaging modalities such as SPECT and PET, composite tomography, ultrasound, magnetic resonance imaging, or even such imaging techniques as radar and combinations thereof. Specific applications for imaging and multi-modality imaging are also provided. Furthermore, anatomical/physiological processes and structures can be modeled with this phantom independent of the modality.

Multiple imaging modalities can be used with the present phantom. For example, the same phantom can be used in different modalities simultaneously (e.g. PET/MR) or in sequence. In another embodiment, the phantom having dual modes: one for imaging moving targets in individual modalities and another mode for multimodality imaging.

In another embodiment, the phantom can be used to test different contrast agents, separately or simultaneously (multiple contrast agents). This includes generic contrast agents that can be used for different imaging modalities or specific contrast agents for specific imaging modalities. Different types of contrast agents can be added to different parts of the torso phantom, e.g., fluid filling the phantom, heart (inside and muscle), aorta, liver, lungs. Specifically, the agents can include, but are not limited to, radioactive isotopes mixable in water for SPECT/PET imaging; salts of heavier elements that change attenuation coefficient of the medium for CT scanning; salts of magnetic materials or magnetic gas e.g., helium-3, for MRI; and microbubbles and/or thickening agents, such as agar or gelatin for ultrasound;

In another embodiment, the phantom also provides technological solutions for a combination of respiratory and cardiac motion in one phantom. Anatomy measurement in the presence of motion, continuous motion imaging and dynamic or static imaging of combined respiratory and cardiac motion are also provided. Other functions for the phantom include, dynamic imaging, flow imaging, diffusion imaging, and stenosis detection.

In another embodiment, the phantom used for image registration. The phantom having fiducial markers both on the outer surface and inside on the heart surface. This is valid for one modality or multimodality. In a preferred embodiment, multimodality motion markers are used. Typical marker diameter is 1-2 mm, and may be larger for multimodality markers.

Other examples of applications for the phantom include but are not limited to, testing MR angiography using helium 3 for looking at lungs and air ducts; imaging flow amount and velocity using MR or ultrasound; imaging mechanical properties of the myocardium using one or any modality; and imaging a partially obstructed aorta 270 in order to model stenosis and taking anatomical or flow measurements.

EXAMPLE 1

Elastic Deformable SPECT/PET/CT Torso Phantom

Most physical phantoms do not model respiratory motion which contributes significantly to image degradation in SPECT and PET scans. We investigated the feasibility of constructing a phantom that mimics respiratory and cardiac cycles in a human allowing acquisition of nuclear medicine data that simulates patient cardiac and respiratory motion. The phantom is used to evaluate algorithms that compensate for these physiological motions that result in mismatch between SPECT/PET and CT data in hybrid systems.

FIGS. 1A and 1C show cartoons of different embodiments that can be used to validate the methods for registering x-ray CT and SPECT data. The phantom for validation should consist of two lung-sized balloons, a heart as described above and shown in FIGS. 2*c*-2*e*, and two sealable internal organs (liver and abdomen). All the parts should be elastic, interconnected, and enclosed in a non-rigid container filled with water. On the top of the body container a number of glass position markers are attached. The myocardium cavity of the heart and the internal organs can be filled with activity independently, allowing for modeling different uptake levels.

A model of the physical phantom is herein described. Referring now to FIG. 1A, two main organs in the phantom are the lungs 130 and the heart 140. Variable number of sealed pouches can be added to model other organs: liver, spleen, gall bladder, kidneys. The organs are held together by elastic mesh and enclosed in an elastic casing. Motion fiducial markers 160 are added to the heart surface and to the outer surface of the phantom.

Lungs are anthropomorphic rubber cavities connected to the "outside world" by air conduits. Control system can supply timed and controlled positive and negative air pressure to the conduit imitating breathing motion or, if needed, stopping breathing at any needed respiratory phase.

Heart model is an enhancement of dynamic heart described by prior art. In a preferred embodiment, two membranes comprised of non-uniform membrane material to provide twisting type of motion (FIG. 1(*b*)) form two independent cavities that can be filled with radioactive liquid of different activity and attenuation levels. Pressure supply to inner cavity (left ventricle) causes heart beating motion is controlled by a control system. Fiducial markers are attached on the heart insert for monitoring motion in either X-ray or emission tomography or both.

Internal organs: Can be filled individually with radioactive and/or attenuating liquids. Other organs should have constant volume.

Fiducial markers: Both attenuating (for CT scan) and emitting motion markers are used. A set of markers attached to the upper surface of the phantom is used to track respiratory motion phases. A set of markers attached to the heart surface is used to track heart motion. We suggest using marker positions for tracking motion and for intermodality registration, especially in PET-CT.

Referring now to FIG. 3, a control system is provided to provide control of the phantom. Central control console is the LabView program running on an attached laptop computer. Heart pumping is done by a modified rodent respirator. Frequency, volume and profile of pumping are controlled by the central console. Lung inflation is done by compressed air from a compressed air tank, deflation is assisted by a vacuum pump. Operation of the vacuum pump and operation of the solenoid valves that control air pressure from the tank is controlled by the central control console. Synchronization between the phantom motion and medical imaging data is achievable through interaction of the phantom central control console and the data acquisition system in the corresponding scanner (e.g. PET-CT or SPECT-CT).

Highly flexible liquid silicone rubber was coated over a cast of a life-sized model. When the cast is removed, the coating forms the lungs of the phantom. These are inflated by a tank of compressed air and deflated by a vacuum pump with the inflation/deflation cycle controlled by computer operated solenoid valves. The heart rests between the inflatable rubber lungs. Changes in the lung volume can cause non-linear deformation of the lung and, to a lesser extent, the heart, the internal organs and attenuating body. Fluid is pumped in and out of the inner most chamber of the heart by a modified rodent respirator. A limit-switch on the respirator provides an R-wave trigger for acquisition of ECG gated data. Two activity filled sealable rubber sacs independently model the liver and the rest of the abdomen with different uptake levels. All parts are elastic, interconnected and enclosed in a non-rigid container filled with water. Glass beads placed on the surface of the phantom act as fiducial markers. Data collection from the phantom is either the snap-shot mode, where the phantom is in one of many repeatable static stages, or the dynamic mode where the phantom 'breathes' and 'beats' continuously.

Figure 6:
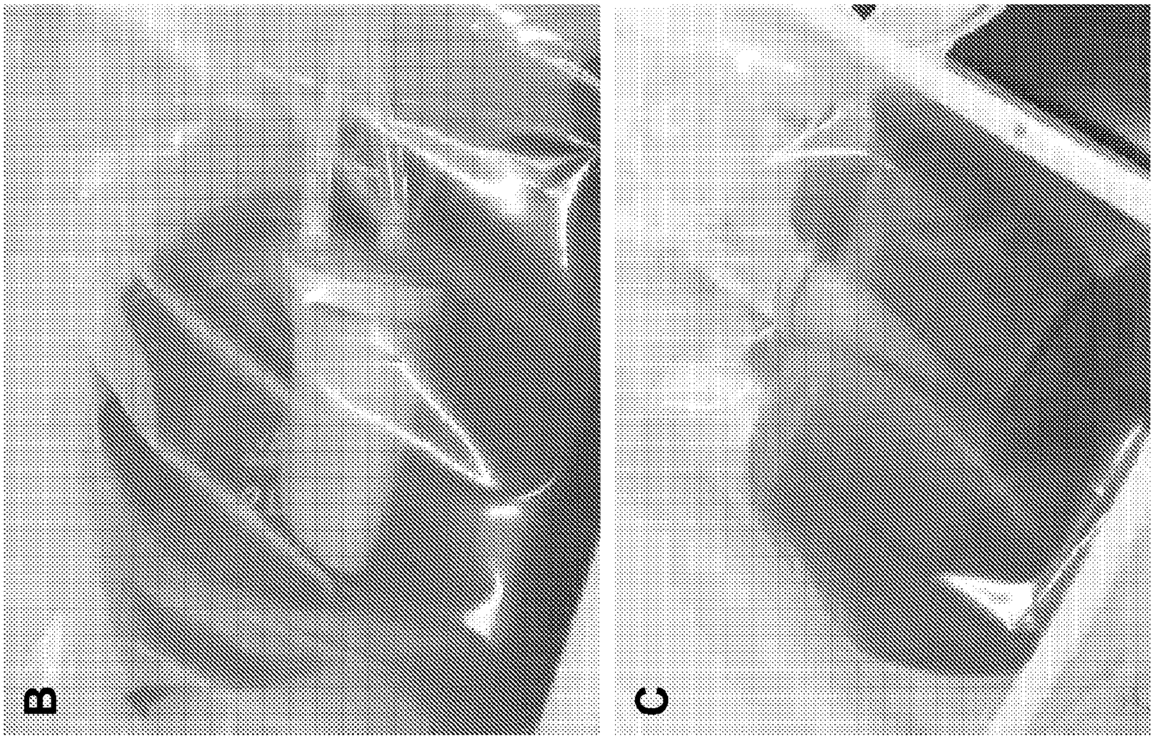
FIGS. 6A, 6B and 6C are photographs of the prototype of the present phantom.
Figure 6:
Figure 7:
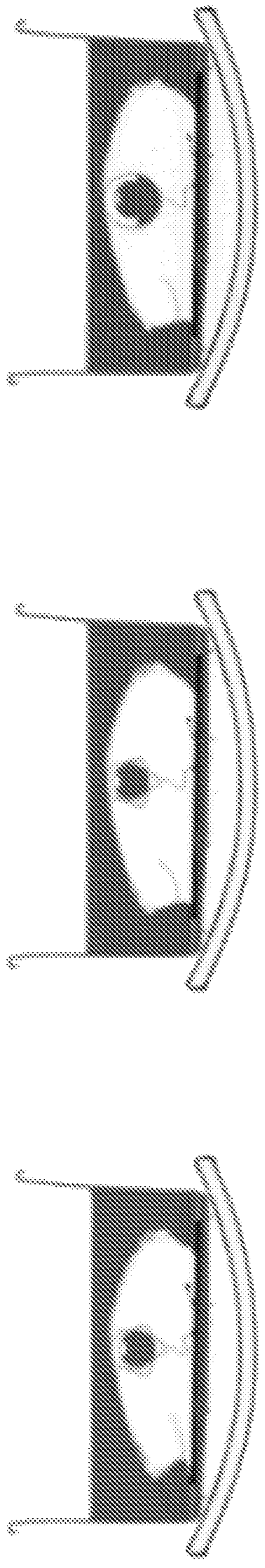
FIG. 7 shows CT image data of the phantom at various stages of inhalation (inflation).
Figure 8:
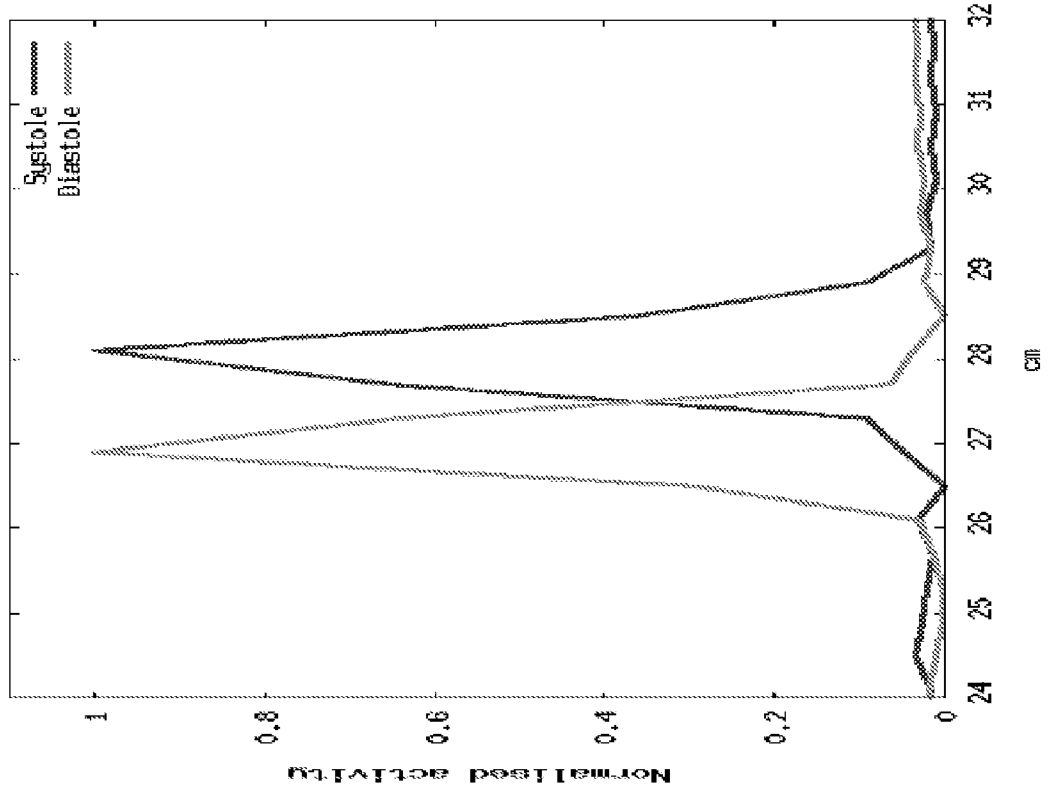
FIG. 8 shows a sinogram of collected data imaging the point source on the heart comparing diastolic and systolic activity.

A prototype of the model phantom was made and is shown in photographs FIGS. 6A, 6B and 6C. Images from the preliminary version of the motion phantom show significant conformation changes in all of the simulated organs. CT image data is shown in FIG. 7 of the phantom prototype at various stages of inhalation (inflation). Sinograms were successfully obtained for both the snap-shot and the dynamic modes, showing that the snap-shot mode allows one to create a database of SPECT/PET sinograms and attenuation maps for the different cardiac and respiratory phases. A sinogram of collected data imaging the point source on the heart comparing diastolic and systolic activity in the prototype phantom is shown in FIG. 8.

Figure 9A:
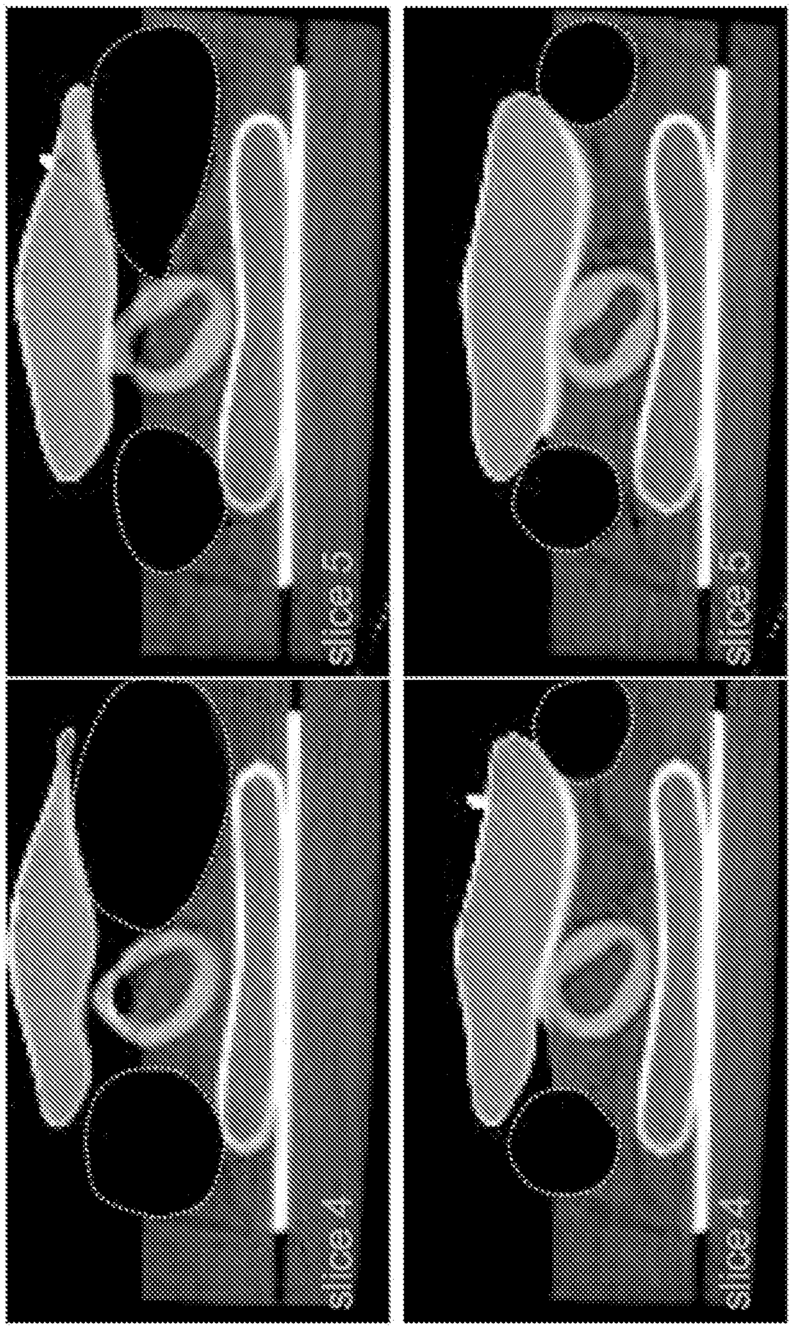
FIG. 9A shows images of a CT scan of inhaled (top row) and exhaled (bottom row) states of the prototype of the elastic motion phantom.
Figure 9B:
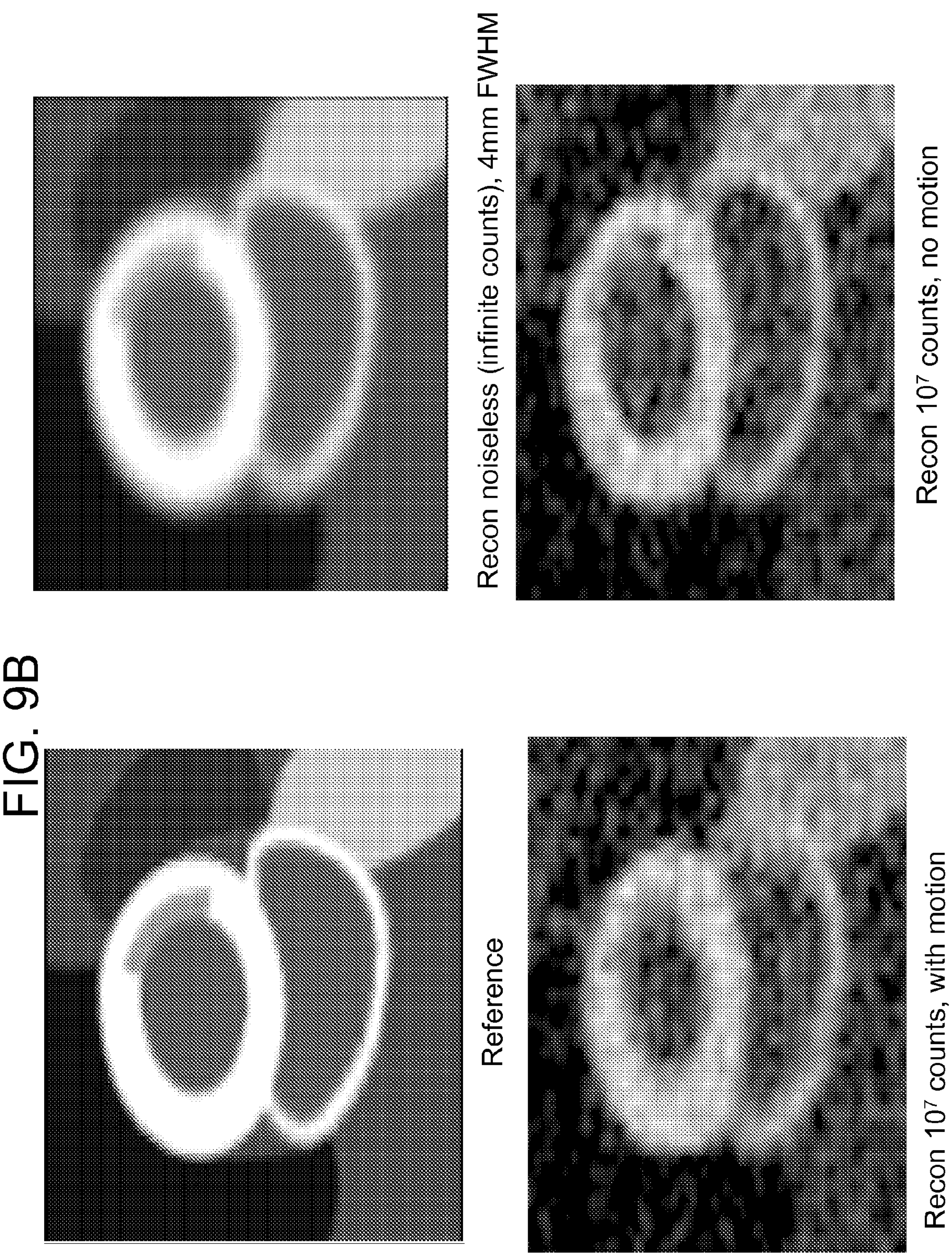
FIG. 9B shows four photographs demonstrating cardiac motion simulation studies. I is the reference, II is taken at $\infty$ counts and 4 mm FWHM, III is taken in motion, $10^7$ counts, and IV is taken with no motion, $10^7$ counts.
Figure 9C:
FIG. 9C shows two photographs demonstrating respiratory motion simulation studies.

FIG. 9A. A prototype deformation phantom used to acquire data at two deformation states. CT scan of inhaled (top row) and exhaled (bottom row) states of the prototype of the elastic motion phantom. Figure illustrates respiration-induced changes in lung volume and in the position of the fiducial that is shown to move from one transaxial slice to another. FIG. 9B shows four photographs demonstrating cardiac motion simulation studies. I is the reference, II is taken at ∞ counts and 4 mm FWHM, III is taken in motion, $10^7$ counts, and IV is taken with no motion, $10^7$ counts. FIG. 9C shows two photographs demonstrating respiratory motion simulation studies. Sagittal cross-section of the phantom showing how shape and position of the lungs, liver and heart change with respiration. Exhaled state is denoted by solid lines, inhaled state is denoted by dashed lines. Approximately 2 cm of respiratory motion between states is shown in the breath-hold MRI.

EXAMPLE 2

Multi-Modality Torso Phantom

Referring to FIG. 1C, the torso phantom can feature a dedicated flow vessel, shown in FIG. 1C as a tube that loops around the heart 140, with a separate plumbing inlet and outlet and separate flow speed/direction control. This opens up the use of the phantom for measuring flow in MRI, ultrasound, radar, etc. In CT, PET, SPECT this will be used as an additional feature.

The phantom of Example 1 was designed specifically for the three mentioned medical modalities. The present Example extends its functionality and applications to include additional imaging modalities as well as radiation therapy planning, as demonstrated in the general description.

The torso phantom of Example 1, can also feature an added elastic string material to the myocardial inlet: bundled strings or sheets, for example, nylon meshes. This will serve a triple purpose: (1) guarantee that the heart muscle does not contract beyond some minimal thickness, (2) help achieve the right mechanical properties of the left ventricle and (3) help create inhomogeneous medium for studying diffusion using MRI. New functions opened up by this improvement include diffusion imaging and imaging elastic properties of the phantom.

The myocardial cavity 340 will have a separate interchangeable inlet 312 and outlet 314 ducts for real-time controlled delivery of the imaging contrast. This allows the use of the phantom for dynamic imaging. Optionally, separate inlet/outlet ducts will be added to the internal organ parts, in order to extend different dynamic imaging applications for imaging these organ models.

Using a system as shown in FIG. 4A, each organ is connected to a reservoir that is controlled by a pump and valve control unit that can be as shown in FIG. 4B.

Fiducial markers attached to the internal organs are supplemented with dosimeters to be used in cancer treatment planning. The fiducial markers can be localized using x-ray or ultrasound, while the dosimeters evaluate radiation dose delivered to the corresponding points in space in the course of operation of the radiotherapy apparatus, thus allowing caparisons between different treatment plans, respiratory gating techniques and motion monitoring methods.

The above examples are provided to illustrate the invention but not to limit its scope. Other variants of the invention will be readily apparent to one of ordinary skill in the art and are encompassed by the appended claims. All publications, databases, and patents cited herein are hereby incorporated by reference for all purposes.

What is claimed:

1. An elastic deformable human torso phantom comprising:

a) a non-rigid torso container containing human organ and tissue models comprising:

(1) two balloons representing the lungs, (2) two membranes, and a base fitted to the membranes representing the heart, said membranes comprising a non-uniform polymer, wherein one membrane is smaller and inserted into a larger membrane to form an inner membrane and an outer membrane, and the base seals the membranes to form an inner cavity in the inner membrane and an outer cavity between the inner membrane and the outer membrane, such that the inner cavity and contents of the inner membrane represents the left ventricle and the outer cavity between the inner membrane and the outer membrane represents the myocardium tissue, wherein the outer cavity is filled with a porous filling, and wherein the non-uniform polymer of both inner and outer membranes of the heart model further comprising at least four ridges 2 to 4 times thicker than the rest of the membrane covering the heart in a spiral manner and completing one full rotation around the membrane, (3) an elastic tube modeling the aorta, and (4) at least two additional models representing internal organs, wherein all said human organ or tissue models are elastic, mechanically interlinked, connected to a control center, encapsulated within a semi-rigid skeletal frame, and enclosed in the non-rigid torso container, wherein the torso container is filled with fluid and then sealed;

b) fiducial markers and/or radiation dosimeters attached to a surface of the torso container and various positions inside the torso container;

c) system for controlled dynamic delivery of contrast agents to each of said internal organ models comprising a plurality of pumps and valves, connecting to outside containers with contrast agents to the corresponding internal organ or tissue models;

d) system for heart and lung motion control comprising one pump for the heart model and either two pumps for simulating lung inhalation and deflation or one pump and a compressed air tank, and further comprising a control box with controllable switches connected to a computer containing software to control the control box and collect R-wave signal generated by the heart model pump.

2. The phantom of claim 1 wherein each cavity of the heart model and the internal organ models each filled with contrast agents of controllable concentrations, thereby allowing for modeling different uptake levels of each organ independently.

3. The phantom of claim 1, wherein the at least four ridges 2 to 4 times thicker than the rest of the membrane covering the heart in a spiral manner and completing one full rotation around the membrane are millimeter-wide.

4. The phantom of claim 1, wherein the fiducial markers are positioned directly on the heart model for tracking simulated heart motion.

5. The phantom of claim 1, wherein the fiducial markers are a multi-Modality fiducial marker system that allows motion tracking and inter-modality registration for single photon emission computed tomography (SPECT), positron emission tomography (PET), x-ray computed tomography (CT), magnetic resonance imaging (MRI) and ultrasound.

6. The phantom of claim 1, wherein the system for heart and lung motion control further comprises pipes connected to said lungs.

7. The phantom of claim 1, further comprising a database of collected images.

8. The phantom of claim 1, wherein the fiducial markers are multi-modality fiducial marker system that allows motion tracking and inter-modality registration for single photon emission computed tomography (SPECT), positron emission tomography (PET) and x-ray computed tomography (CT).

9. The phantom of claim 1, wherein the porous filling comprising a porous polymer or elastic material.

10. The phantom of claim 9, wherein the porous filling comprising a nylon mesh.

11. The phantom of claim 1, wherein radiation dosimeters are attached on the surface of the lung model or other internal organ models and used to measure and optimize the dose distribution in tissue models during radiation therapy procedures.

12. The phantom of claim 1, wherein the system for controlled dynamic delivery of contrast agents to each internal organ model further comprising a control box which regulates delivery of contrast agents to each internal organ model independently from each other.

13. The phantom of claim 1, further comprising an elastic mesh and casing to encase the internal organ models.

14. An elastic deformable human torso phantom comprising:

a) a non-rigid torso container containing human organ and tissue models comprising:

(1) two lung-sized balloons, (2) a heart model comprising two membranes, an inner membrane and a larger membrane, and a base fitted to the membranes thereby sealing the membranes to the base, said membranes comprising a non-uniform polymer material, wherein the inner membrane is inserted into the larger membrane thereby forming an inner cavity between the base and the inner membrane, and an outer cavity between the inner membrane and an outer membrane formed by the larger membrane, wherein the inner cavity and contents of the inner membrane represents the left ventricle and the outer cavity between the inner membrane and the outer membrane represents the myocardium tissue, wherein the outer cavity is filled with porous filling, and wherein the non-uniform polymer of both inner and outer membranes of the heart model further comprising at least four ridges 2 to 4 times thicker than the rest of the membrane covering the heart in a spiral manner and completing one full rotation around the membrane, (3) at least two sealable internal organ models, wherein all the models are elastic, interconnected, connected to a control center, encapsulated within a semi-rigid skeletal frame, and enclosed in the non-rigid torso container, wherein the container is filled with fluid and then sealed;

b) fiducial markers attached to the to and various positions inside the torso container;

c) system for heart and lung motion control comprised of one pump for the heart model and either two pumps for simulating lung inhalation and deflation or one pump and a compressed air tank, and further comprising a control box with controllable switches connected to a computer containing software to control the control box and collect any R-wave signal generated by the heart model pump.

* * * * *